US 6,462,821 B1

(12) United States Patent
Borton et al.

(10) Patent No.: US 6,462,821 B1
(45) Date of Patent: Oct. 8, 2002

(54) DEVELOPABILITY SENSOR WITH DIFFUSE AND SPECULAR OPTICS ARRAY (75) Inventors: Michael D. Borton, Ontario, NY (US); Fred F. Hubble, III, Rochester, NY (US)

(73) Assignee: Xerox Corporation, Stamford, CT (US)

(*) Notice: Subject to any disclaimer, the term of this patent is extended or adjusted under 35 U.S.C. 154(b) by 0 days.

(21) Appl. No.: 09/552,946

(22) Filed: Apr. 20, 2000

(51) Int. Cl.[7] .................. G01N 21/47; G01J 5/02; G03G 15/00
(52) U.S. Cl. .................. 356/446; 356/445; 356/72; 250/353; 250/341.8; 250/358.1; 399/49
(58) Field of Search .................. 356/72, 445, 446, 356/448; 250/353, 341.8, 358.1; 399/49, 53, 74

(56) References Cited

U.S. PATENT DOCUMENTS

| | | | |
|---|---|---|---|
| 4,553,033 A | 11/1985 | Hubble, III et al. | 250/353 |
| 4,950,905 A * | 8/1990 | Butler et al. | 250/358.1 |
| 4,989,985 A | 2/1991 | Hubble, III et al. | 356/445 |
| 5,078,497 A | 1/1992 | Borton et al. | 356/446 |
| 5,083,161 A | 1/1992 | Borton et al. | 399/49 |
| 5,162,874 A * | 11/1992 | Butler | 356/446 |
| 5,519,497 A | 5/1996 | Hubble, III et al. | 356/445 |
| 5,543,923 A * | 8/1996 | Levers et al. | 356/445 |
| 5,666,194 A | 9/1997 | Denton | 356/72 |

* cited by examiner

Primary Examiner—Loha Ben (57) ABSTRACT

A developability sensing system with an optical sensor for measuring the density of imaging material samples on an imaging surface of a printer, with an illumination source and photosensor system for measuring the amount of reflected illumination from the imaging materials. A first lens system and its first photosensor may receive both specularly and diffusely reflected illumination from certain imaging materials. A separate lenslet system is positioned outside of the first lens system. It may comprise one to four spaced apart generally cylindrical lenslets with a central axis generally perpendicular to the imaging material sample and an end surface facing the imaging material sample defined by a segment of a hyperbolic curved surface to form a rotationally symmetrical lens with a hyperbolic cross-section. There are separate photosensors for these lenslets, which are positioned and optically adapted to only receive diffusely reflected light from the imaging material sample, even though reflected illumination from the imaging material sample has both specularly and diffusely reflected illumination from partially specularly reflective imaging materials.

7 Claims, 8 Drawing Sheets

DEVELOPABILITY SENSOR WITH DIFFUSE AND SPECULAR OPTICS ARRAY

Disclosed in the embodiments herein is an improved system and sensor for optically analyzing or measuring the development of imaging material in a printer, for control thereof. In particular, an improved developability sensor for more accurately sensing the development of imaging materials that may have at least partially specular optical properties instead of, or in addition to, diffusely reflective optical properties.

It has been found that some newer types of imaging material, in particular certain color toners for xerographic printers, give partially specular "false diffuse" signals in prior developability sensors. The disclosed embodiment of an improved developability sensor has a low cost and simple optical and sensor system improvement for detecting the diffuse reflections from the control patches of such new toners at an angle and configuration which will not "see" these "false diffuse" specular reflections from such new toners.

By way of background, various types of developability sensors are known in the art for measuring and controlling image development. In particular, it is well known in the art to provide developability sensors for regularly automatically optically analyzing toner-developed test patch areas regularly automatically generated on the surface of the photoreceptor of a xerographic printer, to provide image quality control signals for the controller of that printer. The following Xerox Corp. U.S. patent disclosures are noted by way of providing some known examples and known details which need not be repeated herein: U.S. Pat. Nos. 4,989,985; 4,553,033; 5,083,161; 5,519,497; 5,666,194; and 5,078,497. The latter U.S. Pat. No. 5,078,497 will be referred to by way of background below in connection with explaining problems with such prior systems which the present system addresses. Said U.S. Pat. Nos. 5,083,161, 5,666,194, etc., are also of particular interest for illustration in their FIGS. 2–4, etc., of the general physical configuration of such developability sensors. As so shown, an outer case may have integral molded-in lens elements and the photoemitter and photosensor may be on a circuit board mounted therein.

For reader clarity, the following definitions of terms used in the description of technical background and specific embodiments herein is provided. The terms "printer" or "reproduction apparatus" as used herein broadly encompasses various printers, copiers or multifunction machines or systems, xerographic or otherwise, unless otherwise defined in a claim. Likewise, the type of "developability sensor" in the embodiment herein is a reflective "densitometer" or "toner mass sensor" measuring "DMA" (developed mass per unit area, typically in milligrams per square centimeter). It is more specifically referred to herein as an "ETAC", which is an acronym of "Enhanced Toner Area Coverage" sensor. That is, an "ETAC" may be thought of as one type of "DMA sensor" and also as one type of "developability sensor". An ETAC sensor is an optical, non-contact, sensor and could be used as reflective or transmissive sensor, but is illustrated in the embodiment below as a reflective sensor.

Typically such an ETAC sensor is a small integral unit with a small LED or other, infra-red (IR) light source and lens to illuminate, at a suitable angle (such as 19 degrees), a small area of the imaged surface, and an oppositely angled and positioned sensor lens and photosensor, to provide a variable voltage output proportional to the reflected illumination from a toner test patch on the closely adjacent imaged surface passing by the ETAC. The photosensors may be standard, commercially available, PIN photodiodes or PN photodiodes, mounted in defined locations and areas.

"Developability", in the broad sense, is the end result of the various variable parameters of a printer, which affect the development of an image (including a test patch) on an imaging surface, especially, a toner-developed image area on a xerographic photoreceptor, or on an intermediate transfer belt to which a developed image is transferred before its final transfer to a paper sheet, web, or other final printed substrate. In view of the latter, the "imaged surface", (bearing a "test patch") referred to herein as being examined by the subject developability sensor, will be understood to encompass a photoreceptor, an intermediate transfer surface, or a final substrate surface, unless otherwise indicated. The specific illustrated example herein is a ETAC sensor for sensing colored toner test patches developed on a xerographic photoreceptor of a full color printer.

Such developability sensors for the measurement of toner or other imaging development materials density in a control patch are common elements in mid to high volume copier and printer products. The accuracy of such sensors is particularly important for full color machines. It is also desirable to provide such developability sensing systems with the flexibility and capability for controlling machines with faster process speeds, different photoreceptors, overlaid layers of several different color imaging materials, and/or a variety of image development materials packages.

In that regard, although as noted, devices which optically sense the amount of toner developed on (deposited on) a control patch on a photoreceptor have been commonly used in xerographic machine controls, the reflective properties of the toners being sensed are changing with changes and improvements in developer materials technology. It has been found that toner size, toner composition, the types and sizes of toner material pigments and additives, and the methods of applying them, can all affect the response of a conventional developability sensor. That is, a major current barrier to accurate optical developability sensing is the constantly evolving materials set (toners and their associated constituents of base polymers, pigments, additives, and processing). The optical properties of each part of the new toner can have a dramatic effect on the way a particular developability sensor configuration will react to it.

In particular, the introduction of "flushed pigment" toners has led to a peculiar and misleading response of the above-cited and other types of TAC sensor (a current color DMA sensor). U.S. issued U.S. Pat. Nos. 6,004,714; 5,885,739; 5,866,288; 5,837,409; 5,736,291; 5,723,245; 5,719,002; 5,712,068 and 5,658,704, etc., by Xerox Corp. describe some examples of what are called "flushed pigment" toners, especially those for full color, high speed, printers. A major difference in these toners from predecessor toners is the manner in which the pigments are applied to the base resins. These toners may have a nominal size of about 7 microns, but have dispersed pigment particles which are on the order of only about 0.2 microns. Yet the wavelength of the infrared (IR) light source desirably used in developability sensors is about 0.9 microns.

In previous toners, the pigments were typically applied to the base resins in such a manner that small pigment particles ended up stuck to the outside of the base resin in "clumps". These made the overall surface texture of the toner particles rough and very diffusely reflective. The prior TAC color process control sensor was designed to work with this almost completely diffusely reflective toner material.

In contrast, in flushed pigment toners the pigment disperses across the surface of the base resin particles more evenly so that no large clumps are present, basically forming a monolayer of isolated pigment particles on the surface of the base resin particles. This allows some of the optical properties of the base resin to remain visible through the very thin, semi-transparent surface layer of pigment. Also, the base resin particles may have the form of very small flat platelets or flakes. These resin platelets, even covered by pigment, can provide specular reflections from the platelets which are aligned at the Bragg angle to the TAC illumination source and an area of the TAC photodetector which heretofore was only accessible to diffuse reflections. The result is a small cone of broadened specular reflection off of the faces of the toner particles within a 2° to 5° angle of incidence of the light source. This specular reflection is picked up by the diffuse sensing optics in the TAC, which creates an additional signal in what is supposed to be the diffuse-only photodiode area of the sensor. This produces a non-monotonic output when processed by the sensor's electronics.

Figure 2:
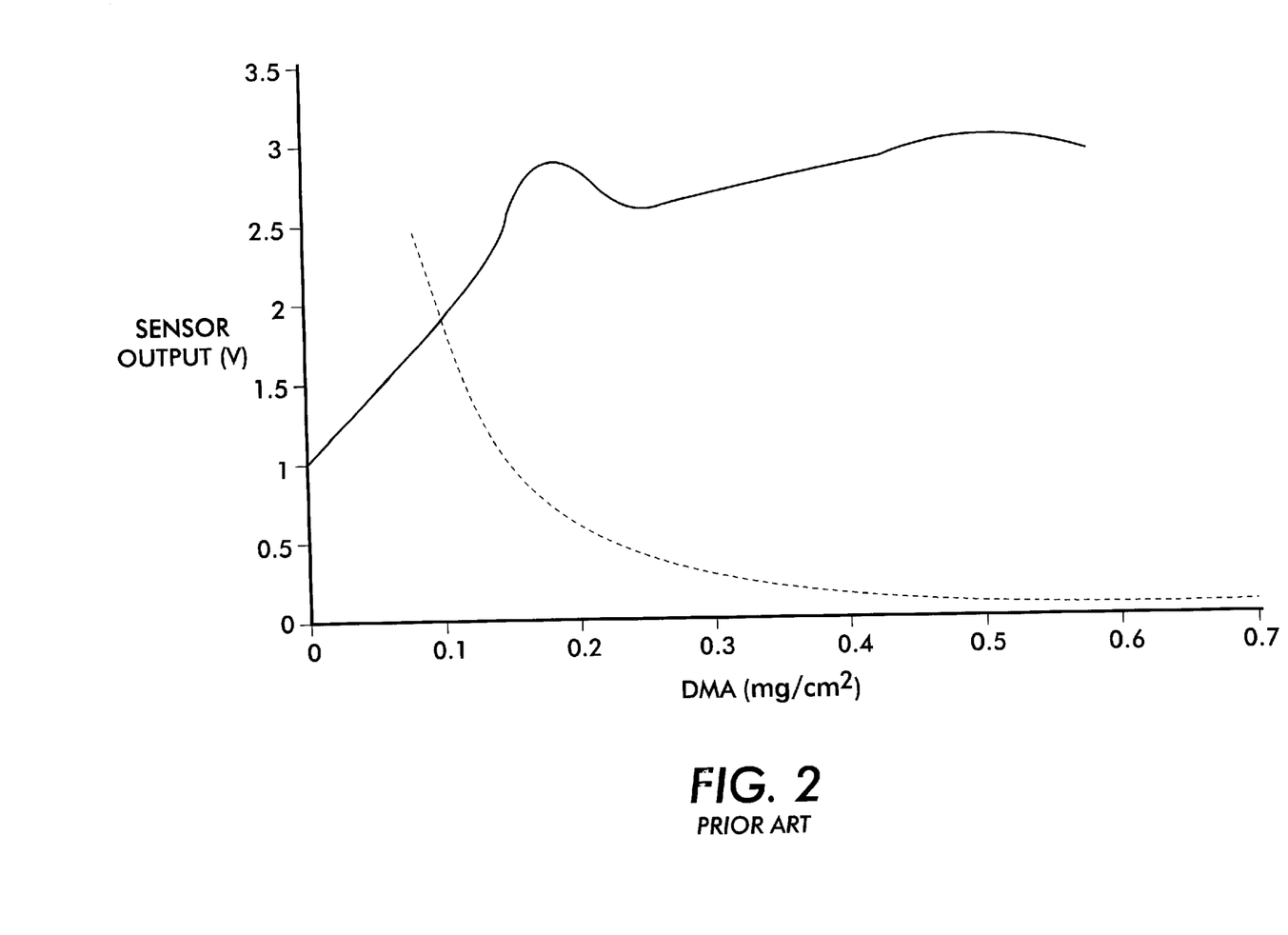
FIG. 2 is a graph showing a deformed electrical signal output of a prior art TAC sensor attempting to measure developability of an exemplary flushed pigment toner, as described above.
Figure 3:
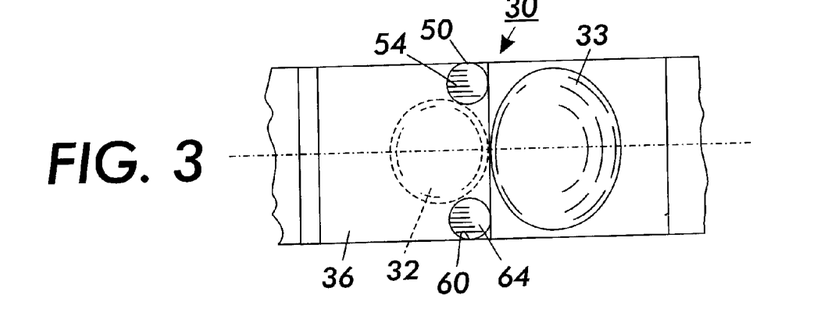
FIG. 3 is an enlarged partial top view of the exemplary improved ETAC sensor per se of FIG. 1, showing the tops of the lenses and lenslets.
Figure 4:
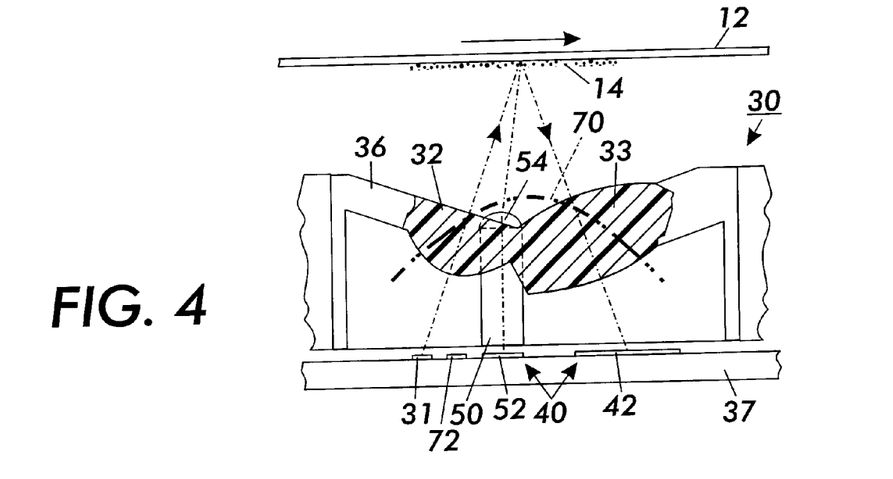
FIG. 4 is a partial side view of the ETAC sensor of FIGS. 1–3, showing a partial side cross-sectional view of the lenses and lenslets.
Figure 5:
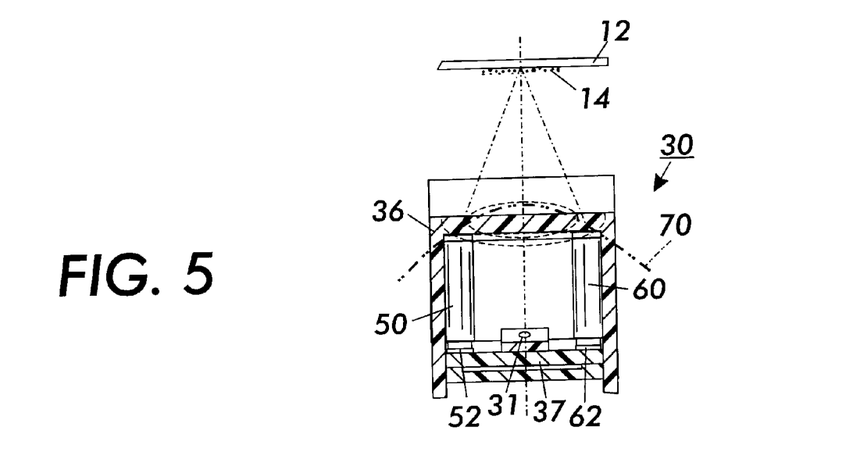
FIG. 5 is a cross-sectional end view of the ETAC sensor of FIGS. 1–4, showing an end view of the lenses and lenslets.
Figure 6:
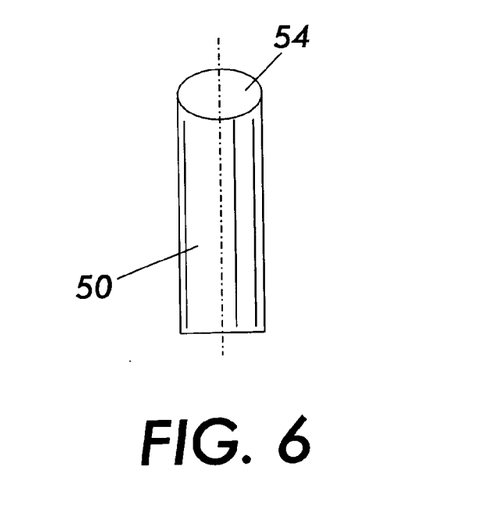
FIG. 6 is a side view of one lenslet per se of the ETAC sensor of FIGS. 1–5.
Figure 7:
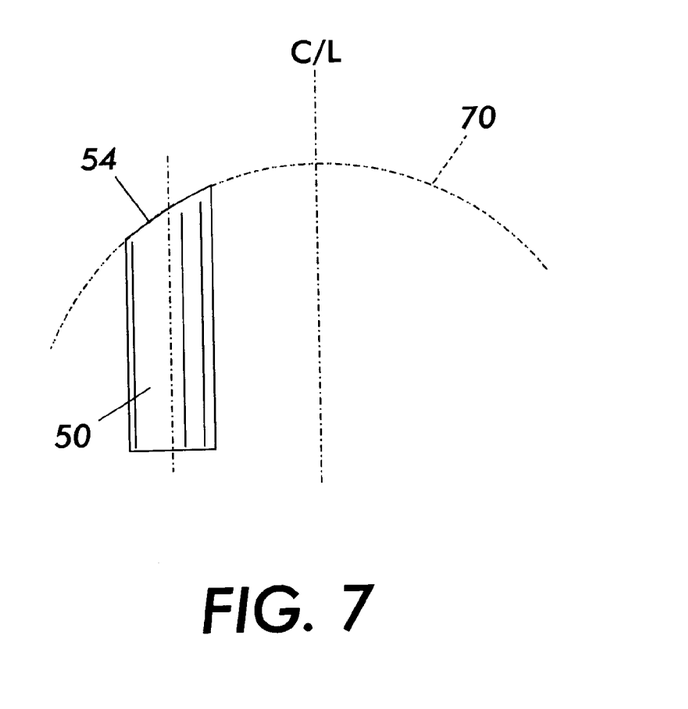
FIG. 7 is a side view of the lenslet per se of FIG. 6 rotated 90 degrees about its central axis.
Figure 8:
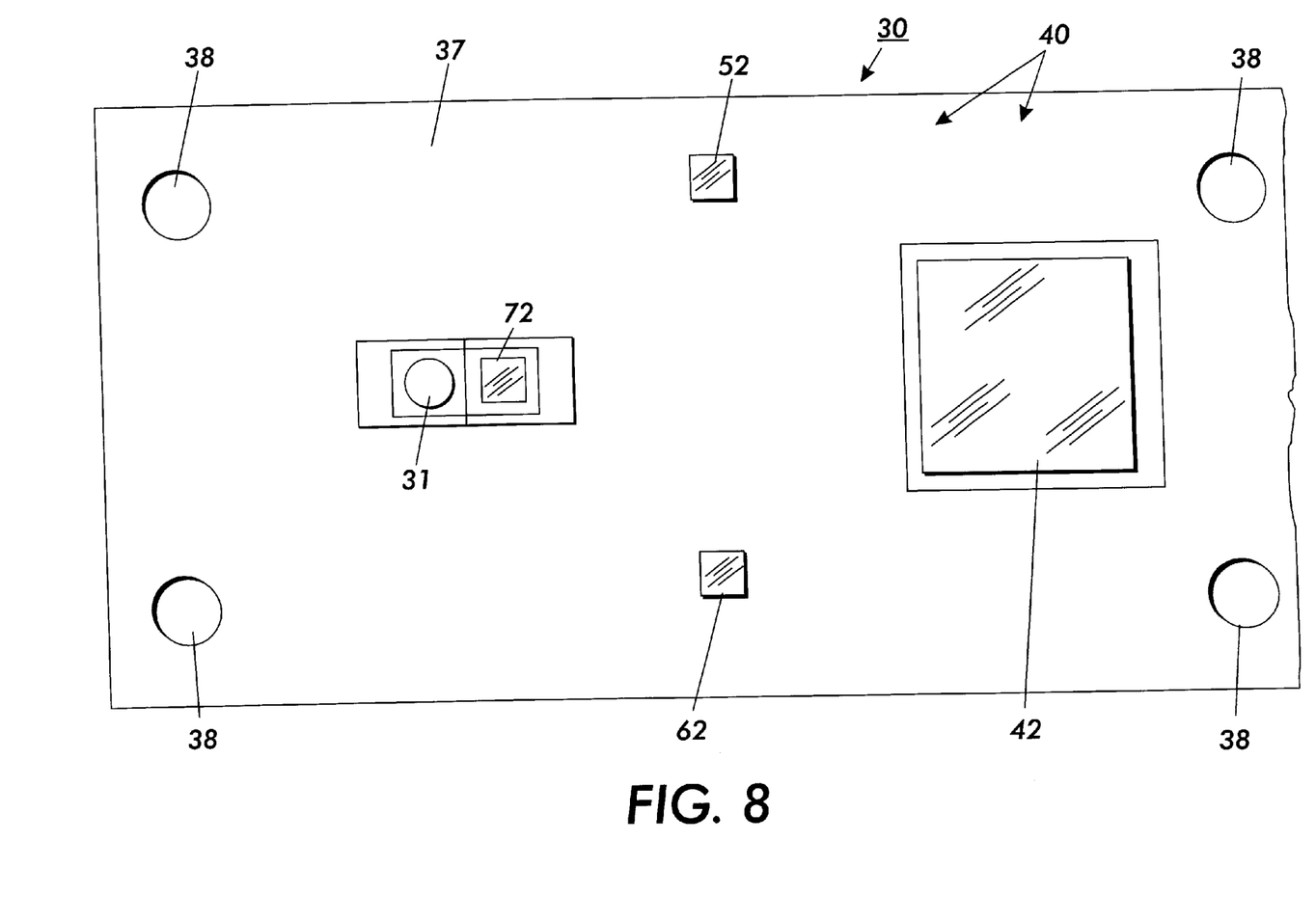
FIG. 8 is a schematic internal top view of the general optical component layout, of the photosensor areas and the LED on the circuit board of the ETAC sensor of FIGS. 1–5, with the normally overlying lenses and lenslets removed.
Figure 9:
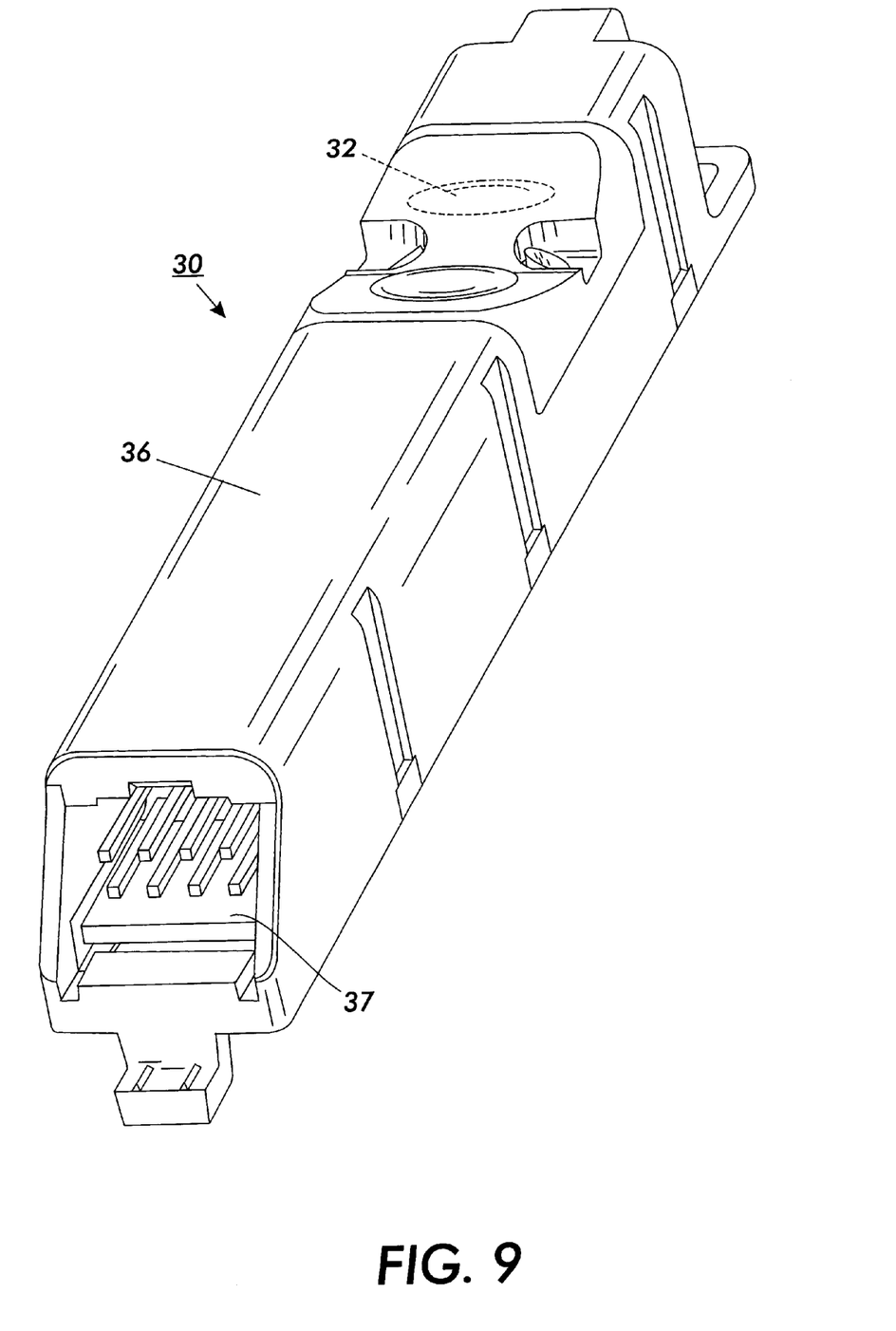
FIG. 9 is a top perspective view of the overall ETAC sensor of FIGS. 1–5.

This problem may be illustrated by reference to an example of the prior TAC sensor implementation with a single collector lens and directly adjacent photosensor areas, as shown in FIGS. 3 and 4 of the above-cited U.S. Pat. No. 5,519,497. The use of flushed pigment toners with such a TAC sensor can cause "false diffuse" specularly reflected light to fall into areas 128 and 130 of the photosensor of FIG. 4 (the same photosensor labeled 106 in FIG. 3 of this U.S. Pat. No. 5,519,497), thus contaminating what was previously only a diffuse signal in those areas 128 and 130. In contrast, with prior, fully diffusely reflecting toners, the only specular reflection collection and signal area was centrally of the center photosensor area 126 of FIG. 4. Thus, for those prior toners, summing the voltage signals from areas 128 and 130 (which are positioned to only receive and measure diffuse reflections from a toner patch) provided a diffuse reflection measurement signal. Subtracting that from the voltage signal from central area 126 provided a specular reflection measurement signal. An example of a resultant non-monotonic deformed output for diffuse reflections of such a prior art TAC sensor attempting to read exemplary flushed pigment toners is shown in the solid line curve on the electrical signal output chart of FIG. 2 of the present application. The dashed-line curve in that FIG. 2 is an exemplary specular reflection measurement signal.

To express this problem with these prior art TAC systems in different words, the area of the prior TAC photodetector that was supposed to be detecting only diffuse reflections from the toner of the toner patch is being optically "contaminated", so as to give a partially false signal reading, by specular reflections from these new and different toners. That is, the previous area of specular reflection is being broadened by additional specular reflections caused by these new toners.

Another potential source of broadened specular reflection may be light from the TAC light source passing through transparent or semi-transparent toner resin and being only weakly scattered by its small, e.g., 0.2 micron, pigments. In that case, part of the light can pass through the toner patch to strike the photoreceptor surface under the test patch. Thus, a portion of the light can be specularly reflected into the single sensor collection lens and subsequently into both the adjacent (edge and central) photodiode sites of the above-described prior TAC.

As disclosed in the embodiment herein, a new developability sensor and optical sensing system has been developed to overcome the deficiencies of the prior TAC sensor to deal with the optical properties of such flushed pigment toners, as well as other possible materials changes or combinations. These new optical sensor properties enable this new sensor to provide monotonic outputs with increasing DMA.

The disclosed embodiment provides a practical and low cost solution for the above-described and other problems of the prior TAC system. The disclosed embodiment of a new developability sensor and its separate lens or lenses system can separately detect only diffuse reflections from the toner control patches at an angle and/or position which will not see this "false diffuse" specular signal from the new toners.

Additional advantages of this disclosed sensor and its new optics include being able to place the detector close to the source, thereby increasing the output signal. Also, having the new optics integrated with minimal interference or redesign with the already proven optics of prior art TAC developability sensor systems, such as those discussed above.

One specific feature of the specific embodiment disclosed herein is to provide, in an optical developability sensing system with an optical sensor for measuring the density of imaging material on an imaging surface of a printer, wherein said optical sensor includes an illumination source for directing illumination to an imaging material sample on an imaging surface and a photosensor system for measuring the amount of reflected illumination therefrom, the improvement in said optical developability sensing system optical sensor; wherein said imaging materials are partially specularly reflective and said reflected illumination from said imaging material sample has both specular and diffusely said reflected illumination, said photosensor system includes a first lens system with a first optical axis relative to said imaging material sample and a first photosensor optically associated with said first lens system receiving both said specular and diffusely said reflected illumination from said imaging material sample, a separate lenslet system positioned outside of said first lens system and substantially laterally optically offset at a substantially greater angle from said first optical axis of said first lens system relative to said imaging material sample, a separate second photosensor optically associated with said separate lenslet system, said separate lenslet system and said optically associated separate second photosensor being optically adapted to only receive diffusely reflected light from said imaging material sample on said imaging surface, even though said reflected illumination from said imaging material sample has both specular and diffusely said reflected illumination from said partially specularly reflective imaging materials.

Further features disclosed in the embodiment herein, individually or in combination, include those wherein said separate lenslet system comprises at least one lenslet with a surface facing said imaging material sample and said imaging surface, which lenslet surface is defined by segments of a hyperbolic curved surface to form a rotationally symmetrical lens with a hyperbolic cross-section; and/or wherein said separate lenslet system comprises at least one lenslet in the form of an elongated generally cylindrical optically conductive plastic member; and/or wherein said separate lenslet system comprises at least two oppositely spaced apart lenslets; and/or wherein said separate lenslet system comprises at least one elongated generally cylindrical lens with a central axis generally perpendicular to said imaging material sample and said imaging surface; and/or wherein said central axis of said elongated generally cylindrical lens is at a substantial angle to said first optical axis of said first lens system; and/or wherein said central axis of said elongated generally cylindrical lens is at an angle of approximately 19 degrees to said first optical axis of said first lens system.

The disclosed system and sensor may be utilized in various printing control systems and operations. It is well known and preferable to program and execute imaging, printing, and other control functions and logic with software instructions for conventional or general purpose microprocessors, as taught by numerous prior patents and commercial products. Such programming or software may of course vary depending on the particular functions, software type, and microprocessor or other computer system utilized, but will be available to, or readily programmable without undue experimentation, from functional descriptions, such as those provided herein, and/or prior knowledge of functions which are conventional, together with general knowledge in the software or computer arts. Alternatively, the disclosed control system or method or parts thereof may be implemented partially or fully in hardware, using standard logic circuits or single chip VLSI designs.

As to specific components of the subject apparatus or methods, or alternatives therefor, it will be appreciated that, as is normally the case, some such components are known per se in other apparatus or applications which may be additionally or alternatively used herein, including those from art cited herein. All references cited in this specification, and their references, are incorporated by reference herein where appropriate for teachings of additional or alternative details, features, and/or technical background. What is well known to those skilled in the art need not be described herein.

Various of the above-mentioned and further features and advantages will be apparent to those skilled in the art from the specific apparatus and its operation or methods described in the example below, and the claims. Thus, the present invention will be better understood from this description of this specific embodiment, including the drawing figures (which are approximately to scale) wherein:

Figure 1:
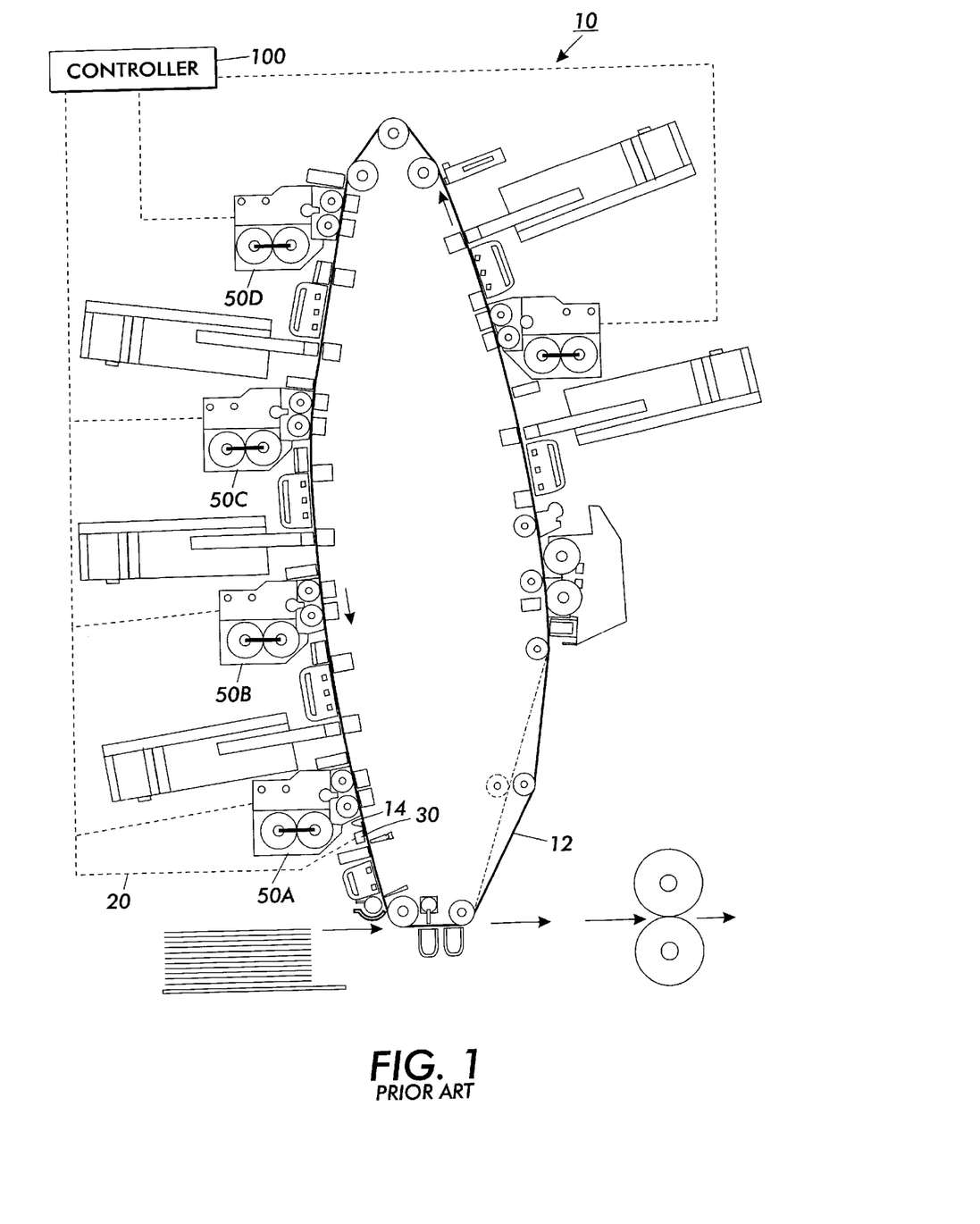
FIG. 1 is a schematic view of one example of a color xerographic printer in which one example of a subject improved ETAC system may be mounted to sense developability by sensing toner test toner patches generated and developed on the photoreceptor in a known manner.

Describing now in further detail the exemplary embodiment with reference to the Figures, there is shown in FIG. 1 as an exemplary reproduction machine a color printer 10 with a photoreceptor 12. The photoreceptor 12 has "flushed pigment" toner test patches 14 generated and developed thereon in a well know manner by a machine controller 100 controlling the different color developer units 50A, 50B, 50C, and 50D. The printer 10 illustrated in FIG. 1 is one type of full color xerographic printer, which may employ an IOI (image on image) system, otherwise known as a READ (recharge and develop) and/or color-on-color (multilayer toner) image development system, as described in prior patents under those known descriptive terms. However, the present invention is not limited thereto. The operation of various suitable full color or other exemplary xerographic printers is well known in the art, and need not be described herein. This illustration of a printer 10 is merely for illustrating one example or application of controlling a color printer with a developability sensing system 20, which, as described above, is generally known.

The developability sensing system 20 here includes one or more exemplary ETAC developability sensors 30 positioned adjacent to the photoreceptor 12 (the imaged surface here) for optically sensing toner density in the test patches 14 as the test patches pass under an ETAC sensor 30. In the example of FIG. 1, three ETAC sensors 30 may be located in the same basic position, after the last development station 50A, but transversely spaced laterally (transversely) across the width of the photoreceptor 12. Test patches 14 from different developer units may be generated for those different lateral positions of the ETAC's. Alternatively, the ETAC's 30 could be staggered vertically or in some combination thereof.

The output signals from the ETAC sensors 30 may be used to maintain and control developability by controlling the connecting printer 10 controller 100, in a known manner. This exemplary ETAC sensor 30 may be generally similar in general operation, except as to important differences described herein, to that shown or described in the above-cited U.S. Pat. Nos. 5,666,194 and 4,989,985 and/or 5,078,497.

As noted, the exemplary ETAC sensor 30 may conventionally be a small integral unit with a small, LED 31 or other infra-red (IR) light source, collimated by a simple lens 32 at a suitable angle to the surface of the photoreceptor 12 to illuminate a small area thereof. In particular, illuminating part of a test patch 14 moving on the photoreceptor 12 surface past the closely adjacent ETAC 30. A suitable such angle has been found to be 19 degrees from the centerline perpendicular to the plane of the photoreceptor 12 surface, or 71 degrees from the plane of the photoreceptor 12 surface. There is an oppositely angled and positioned light collector lens 33. A photosensor array 40 in the ETAC 30 looks at that illuminated area of the test patch 14 to provide a variable voltage output proportional to the reflected illumination from the toner test patch 14. All of the photosensors of the photosensor array 40 may all be well known, standard, commercially available, PIN or PN photodiodes, mounted in defined locations and areas to be further described below.

Turning now to differences between this ETAC sensor 30 and the prior art TAC sensors described in the above-cited patents, it will be seen, especially from FIGS. 3–8, etc., that this ETAC sensor 30 has two special small diameter lenslets 50 and 60 spaced on opposite sides thereof, outside of the central photodiode area 42 and its collector lens 33. That collector lens 33 and its central photodiode area 42 captures both specular and diffuse reflections from the test patch 14, as previously described.

These lenslets 50, 60 are separate from, spaced from, and very distinct from, the collector lens 33. As shown individually in FIGS. 6 and 7, as well as in other FIGS., each lenslet 50, 60 may comprise an elongated cylindrical tube functioning as light pipe optically connecting at its bottom end with a respective small photodetector 52 and 62. Each lenslet has a respective specially curved upper lens surface 54, 64 defined by and conforming to the dashed line hyperbolic curved surface 70 illustrated in FIGS. 4, 5 and 7. That is, the respective upper surfaces 54 and 64 of the lenslets 50 and 60 are segments of that hyperbolic curved surface 70, forming a rotationally symmetrical lens with a hyperbolic cross-section. That is, the lenslet lens surfaces 54, 64 are small real surface sections of this imaginary curved surface 70 at their respective intersection positions therewith out on that surface 70. This curved surface 70 is centered on the unit and centered on the illumination area of the test patch, and the lenslets are substantially spaced from that center line. The central axis of each of the lenslets here is parallel to the centerline of the surface 70, that is, also perpendicular to the test patch (which is, of course, in the plane of the photoreceptor surface).

These lenslet 50, 60 lens surfaces 54, 64, and the more outer spaced positions of these lenslets 50, 60, at a greater angle insure capturing only parts of the diffuse component of the reflection from the test patch 14 in the lenslets. That is, the lenslets 50, 60 do not capture any specular reflections from even flushed pigment toners. The cylindrical body of the lenslets 50, 60 then internally reflects and conducts the captured light from its surfaces 54, 64 down to respective separate photodetectors 52 or 62, to provide signals more accurately proportional to the amount of toner in the test patch 14 area being illuminated by the LED 31.

Figure 10:
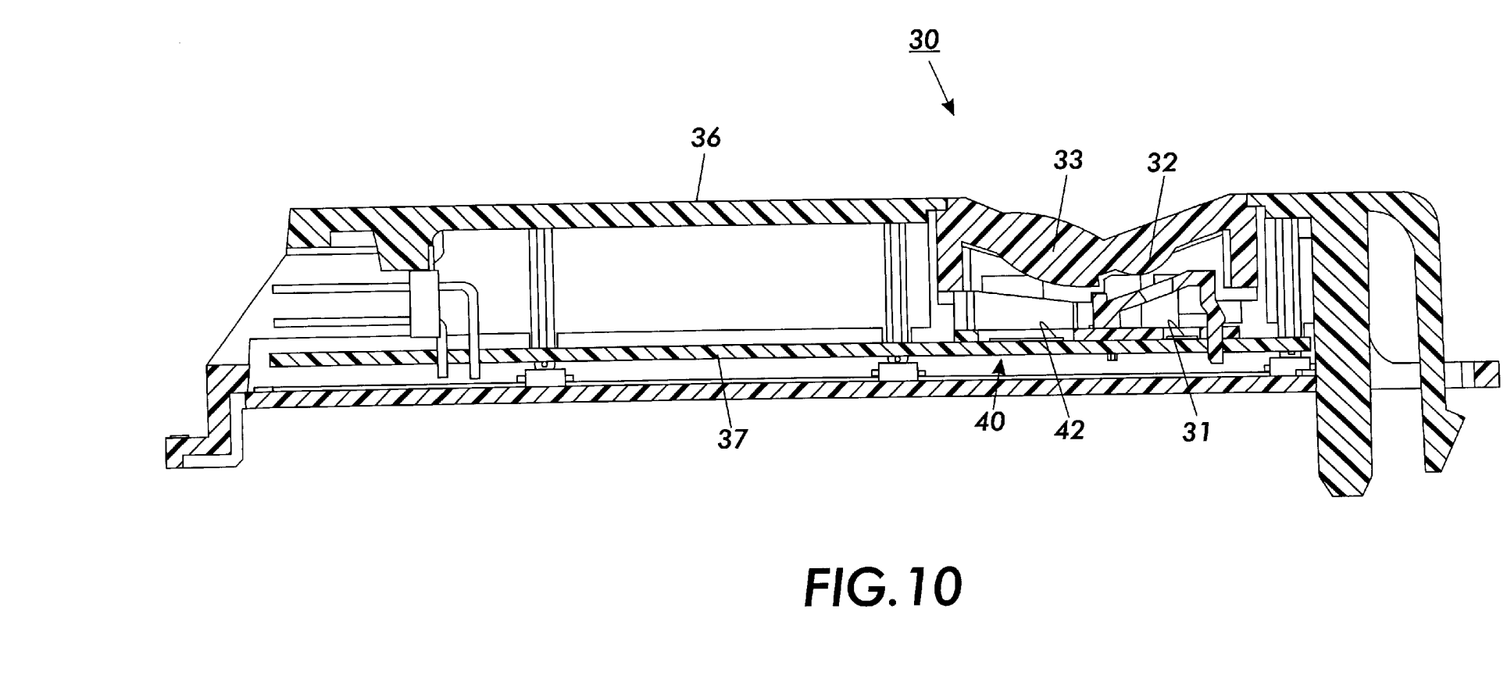
FIG. 10 is a full central cross-sectional view of the ETAC sensor of FIG. 9.
Figure 11:
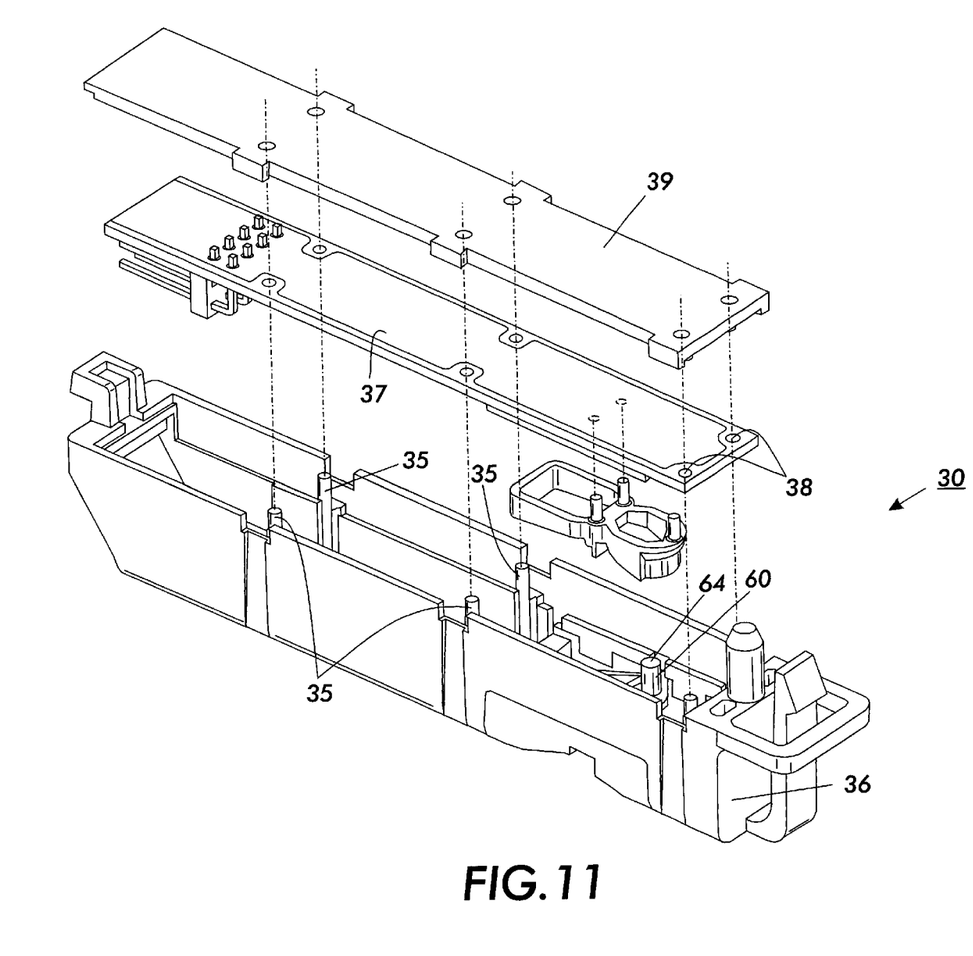
FIG. 11 is an upside down exploded view of the ETAC sensor of FIGS. 9 and 10 showing the cover unit with its integral molded lenses, the internal circuit board, and the bottom cover, separated from one another.

The ETAC unit 30 housing 36 may be a single plastic molding with all of the lens and lenslets integrally molded therein, as particularly shown in FIGS. 10 and 11. The plastic of this housing 36 is desirably visibly pigmented black with an organic dye, so as to block visible light but transmit the above-indicated IR through all of the lenses and lenslets. For example, a commercially available Autohaus V825 plastic material with their E830 additive.

As particularly shown in FIG. 11, this ETAC housing 36 may also have molded in pins 35 or other means for aligning and removably mounting therein the circuit board 37 containing and mounting the LED and all the photosensors and electronics. The pins 35 may mate with alignment holes such as 38 in the circuit board 37. The bottom of the ETAC unit 30 may have a simple bottom cover 39 snapping onto the bottom of the housing 36.

This disclosed embodiment of a new ETAC developability sensor 30 detects the diffuse reflections from the toner control patches 14 at an angle and position which will not see the "false diffuse" specular signal from the new toners. The position chosen for the light gathering position of the lenslets 50, 60 is at 90° to (perpendicular to) the test patch plane.

Further advantages of this position include placing the detector closer to the source, thereby increasing the output signal. Also, the illustrated positions fit these new optics into the same small confined area with minimal interference or redesign of the already proven optics of the prior art TAC systems.

As is previously known, and taught for example in the above-cited U.S. Pat. No. 4,553,033 (note it's reference numbers 84 and 104), an additional feedback photodiode 72 (as shown here in the LED and photosensors component circuit board layout of FIG. 8 here), may be used to collect a small portion of the LED flux output for the purpose of controlling that flux with a suitable control circuit controlling the current or voltage to the LED to keep it constant.

It will be appreciated that while two of the above-described light gathering rods or lenslets 50, 60 and their associated photosensors 52, 62 are shown, that it is not essential to have two. Having two, laterally spaced apart as shown, does, however, desirably also increases the tolerance of the entire ETAC unit to longitudinal angular mounting misalignment. However, two more such lenslet sub-systems (to provide a total of four), spaced apart on the other axis of the ETAC unit, would provide that same mounting alignment tolerance advantage for both axes of the ETAC unit.

While the embodiment disclosed herein is preferred, it will be appreciated from this teaching that various alternatives, modifications, variations or improvements therein may be made by those skilled in the art, which are intended to be encompassed by the following claims.

What is claimed is:

1. In an optical developability sensing system with an optical sensor for measuring the density of imaging material on an imaging surface of a printer, wherein said optical sensor includes an illumination source for directing illumination to an imaging material sample on said imaging surface and a photosensor system for measuring the amount of reflected illumination therefrom, the improvement in said optical developability sensing system optical sensor wherein;

said imaging material is partially specularly reflective and said reflected illumination from said imaging material sample has both specularly and diffusely reflected illumination, said photosensor system includes a first lens system with a first optical axis relative to said imaging material sample and a first photosensor optically associated with said first lens system receiving both said specularly and diffusely reflected illumination from said imaging material sample, a separate lenslet system positioned outside of said first lens system and substantially laterally optically offset at a substantially greater angle from said first optical axis of said first lens system relative to said imaging material sample, a separate second photosensor optically associated with said separate lenslet system, said separate lenslet system and said optically associated separate second photosensor being optically adapted to only receive diffusely reflected light from said imaging material sample on said imaging surface, even though said reflected illumination from said imaging material sample has both specularly and diffusely reflected illumination from said partially specularly reflective imaging material.

2. The optical developability sensing system of claim 1, wherein said separate lenslet system comprises at least one lenslet with a surface facing said imaging material sample and said imaging surface, which lenslet surface is defined by segments of a hyperbolic curved surface to form a rotationally symmetrical lens with a hyperbolic cross-section.

3. The optical developability sensing system of claim 1, wherein said separate lenslet system comprises at least one lenslet in the form of an elongated generally cylindrical optically conductive plastic member.

4. The optical developability sensing system of claim 1, wherein said separate lenslet system comprises at least two oppositely spaced apart lenslets.

5. The optical developability sensing system of claim 1, wherein said separate lenslet system comprises at least one elongated generally cylindrical lens with a central axis generally perpendicular to said imaging material sample and said imaging surface.

6. The optical developability sensing system of claim 5, wherein said elongated generally cylindrical lens has an end surface facing said imaging material sample and said imaging surface which is defined by a segment of a hyperbolic curved surface to form a rotationally symmetrical lens with a hyperbolic cross-section, and wherein said central axis of said elongated generally cylindrical lens is at a substantial angle to said first optical axis of said first lens system.

7. The optical developability sensing system of claim 5, wherein said central axis of said elongated generally cylindrical lens is at an angle of approximately 19 degrees to said first optical axis of said first lens system.

* * * * *